United States Patent
Haas

(10) Patent No.: US 8,367,086 B1
(45) Date of Patent: Feb. 5, 2013

(54) PROCESS AND PRODUCT FOR INHIBITING OR PREVENTING BACTERIAL INFECTIONS

(75) Inventor: Gerhard J. Haas, Woodcliff Lake, NJ (US)

(73) Assignee: S.S. Steiner, Inc., New York, NY (US)

( * ) Notice: Subject to any disclaimer, the term of this patent is extended or adjusted under 35 U.S.C. 154(b) by 869 days.

(21) Appl. No.: 11/434,660

(22) Filed: May 17, 2006

Related U.S. Application Data

(63) Continuation-in-part of application No. 10/991,221, filed on Nov. 18, 2004, now Pat. No. 7,641,923, which is a continuation-in-part of application No. 10/769,654, filed on Feb. 2, 2004, now Pat. No. 7,364,747.

(51) Int. Cl.
 *A01N 25/00* (2006.01)
 *A61K 31/497* (2006.01)
(52) U.S. Cl. ........................ 424/405; 514/253
(58) Field of Classification Search .................. 424/405; 514/253
 See application file for complete search history.

(56) References Cited

U.S. PATENT DOCUMENTS

| | | | | |
|---|---|---|---|---|
| 2,963,406 | A | * 12/1960 | Bockelmann et al. | 435/244 |
| 4,148,873 | A | * 4/1979 | Owades | 424/59 |
| 5,597,560 | A | * 1/1997 | Bergamini et al. | 424/78.04 |
| 5,668,147 | A | * 9/1997 | Nakano et al. | 514/312 |
| 6,319,958 | B1 * | 11/2001 | Johnson et al. | 514/739 |
| 6,451,365 | B1 * | 9/2002 | King et al. | 426/326 |
| 7,195,785 | B2 * | 3/2007 | Babish et al. | 424/725 |
| 2003/0013773 | A1 * | 1/2003 | Haas | 514/690 |
| 2003/0206940 | A1 * | 11/2003 | Gott et al. | 424/443 |

FOREIGN PATENT DOCUMENTS

WO WO03/000185 * 1/2003

OTHER PUBLICATIONS

Simpson et. al. (Journal of Applied Bacteriology (1992) 72:327-334).*

* cited by examiner

*Primary Examiner* — Marcos Sznaidman
(74) *Attorney, Agent, or Firm* — Walter D. Ames

(57) ABSTRACT

A process for inhibiting or preventing bacterial infections in animals by administering a mixture of a hop composition and an antibiotic selected from the group consisting of polymyxin, ciprofloxacin and tobramycin.

16 Claims, No Drawings

PROCESS AND PRODUCT FOR INHIBITING OR PREVENTING BACTERIAL INFECTIONS

This application is a continuation-in-part of my application Ser. No. 10/991,221. filed on Nov. 18, 2004 now U.S. Pat. No. 7,641,923 and entitled, Process and Product for Inhibiting or Preventing Bacterial Infections, which itself is a continuation-in-part of my application Ser. No. 10/769,654, filed on Feb. 2, 2004 now U.S. Pat. No. 7,364,747. As to all subject matter in common with either or both of those applications, which are specifically incorporated by reference herein, I claim the benefit of their earlier filing dates with respect thereto.

FIELD OF THE INVENTION

The invention presented herein generally relates to processes and products for inhibiting bacteria which cause infections in animals, including human beings, either by treating subjects having a bacterial infection, or treating those susceptible to such infections. More specifically, it concerns processes and products for treating infected or susceptible animals with a mixture of a hop composition and an antibacterial composition.

BACKGROUND OF THE INVENTION

The individual compositions processes utilizing and mixtures of which constitute the present invention, are well known individually. Thus, polymyxin compositions, most notably polymyxin B, are recognized anti-bacterial compounds. Polymyxin B is a cyclic polypeptide produced and secreted by *Bacillus polymyxa*. The anti-bacterial effect of this antibiotic is apparently based on its ability to increase the permeability of the cell wall of bacteria. This creates channels in the cell membrane, resulting in the leakage of small molecules, such as phosphates, out of the bacterial cell. However, polymyxin B's spectrum of activity is recognized as being limited to gram-negative rods, such as *Pseudomonas, E. coli, Enterobacter, Klebsiella, Salmonella* and *Shigella*. The Proteus group is resistant, as are gram-negative cocci and all gram-positive bacteria, in common with yeast and fungi. Apparently the thickness of the cell wall of bacteria affects the ability of polymyxin to permeate the wall and reach the cell membrane.

Polymyxins are produced by the growth of *Bacillus polymyxa*. A plurality of isomers are found to be present, and thus the family of polymyxins is presently known to consist of polymyxin A, B, C, D and E, the last named also being known by the by the name, colistin. However, polymyxin B is most commonly used. It is quite water soluble and is stable such that a solution of polymyxin B can be maintained under refrigeration for one year without the loss of substantial antibacterial activity. While the individual experiments on which the present invention is based have taken place using polymyxin B, which has the greatest anti-bacterial activity of the polymyxins, when the term, polymyxin composition is used herein, it is intended that it cover not only polymyxin B, but other polymyxins such as polymyxins A and E.

Ciprofloxacin, sometimes marketed in the form of its HCl salt, is another well-known antibiotic. It is a broad spectrum antimicrobial agent that is active again certain, but not all Gram-positive and Gram-negative bacteria, including anthrax. Chemically it is a fluoroquinolone; in acid form it is 1-cyclopropyl-6-fluoro-1,4-dihyro-4-oxo-7-(1-piperaznyl)-3-quinolinecarboxylic acid. It is marketed under the trademark CIPRO as the monohydrochloride, monohydrate salt of the acid. As used herein, the term, ciprofloxacin will be used to refer to both the acid and its salt. It is believed to stop the multiplication of bacteria by inhibiting the reproduction and repair of their DNA.

Tobramycin is another broad spectrum antibiotic, categorized as an aminoglycoside. Its chemical formula is O-3-amino-3-deoxy-α-D-glucopyranosyl-(1☐4)-O-[2/6-di-amino-2,3,6-trideoxy-α-D-ribo-hexopyransol-(1☐6)]-)]-2-deoxy-L-streptamine. While it is used to treat a variety of bacterial infections, it has found a special use in treating eye infections, alone or as a combination product in the form of a suspension or ointment.

The other, basic ingredient that forms the basis of my antibacterial composition and process is a hops composition. The hops plant, *Humulus lupulus*, is a twining vine that is a member of the mulberry family (Cannabinaceae). The female hop plant has inconspicuous flowers, and forms glandular, cone-shaped catkins which, when ripe and dried, find familiar use to impart a bitter flavor to beverages derived from malt. Hop has been used to flavor and preserve wort and beer since the 12th century in Germany and the 15th century in England. Its resins, which reside in the yellow glands of its cones, are known to possess antimicrobial properties. Those resins are extracted from the cones, usually by supercritical carbon dioxide treatment or by extraction with organic solvents. Today they, or in their preisomerized form, are frequently added for the bittering of beer in place of the hop flowers and hop pellets previously utilized.

With respect to the chemical nature of hop compounds, these are weak acids classified as alpha and beta resins or bitter acids. Alpha bitter acids are represented by humulone and its cogeners, cohumulone, adhumulone, prehumulone and posthumulone. The beta resins are represented by lupulone, often referred to as lupulon, and its cogeners, colupulone, adlupulone, and prelupulone. The alpha and beta acids have alicyclic structures (2,4-cyclohexodine-1-one), but their cogeners differ in the nature of the acyl side chains. While the alpha acids and their derivatives, the iso acids, contribute most to the bitterness of beer, there are many other, sometimes minor constituents that contribute to preservation and bitterness. One of these compounds is xanthohumol, a compound that falls within the scope of the present invention.

The antimicrobial properties of hop compounds are well-known; their extracts having been used to inhibit the growth of most gram positive microbes, and they are usually inactive against gram negative microbes. Yeast is not inhibited by hop compounds. Fungi are either not inhibited or inhibited only at unfavorably high concentrations of hop extracts. As the term, hop composition, is used herein, it is meant to cover the primary hop compounds, humulone, lupulone as well as xanthohumol, and their cogeners and isomers, either in pure form or as extracts, as well as iso and other derivatives and mixtures of the above.

SUMMARY OF THE INVENTION

Whether in the form of a process for preventing or inhibiting the growth of bacteria or as a composition that is useful in inhibiting bacterial growth, the present invention is based on the unexpected finding that there is synergism between any of three different antimicrobial agents, polymyxin, ciprofloxacin and tobramycin, on the one hand, and hop compositions, on the other, in inhibiting bacteria that greatly exceeds their individual antibacterial capacities. While the reason for such cooperation is not known, the results of the antibacterial activity of a mixture of polymyxin/hop, ciprofloxacin/hop and tobramycin/hop compositions are apparent, surprising and nonobvious.

In its process form, my invention may be broadly defined as a process for inhibiting the growth of bacteria in an animal, which term includes the genus *homo sapiens*, so infected, by treating the animal with an antibacterial composition, which comprises administering to the animal a pharmacologically effective amount of a mixture of a polymyxin composition and a hop composition, or a ciprofloxacin/hop, or a tobramycin/hop composition, whereby the mixture has a positive co-action or synergistic effect on the infection that is greater than the antibacterial effect of the polymyxin, or ciprofoxacin or tobramycin or hop composition separately administered. The bacteria toward which the ultimate composition or mixture is directed are usually gram positive, but some compositions according to my invention have been found to have definite synergistic activity against some gram negative organisms as well.

More specifically defining the process of my invention, the polymyxin compound that will preferentially be utilized is polymyxin B. Even more specifically, the preferred polymyxin is polymyxin B sulphate. The ciprofoxacin may be in the form of ciprofloxacin HCL.

With respect to the hop compounds that find ready use in the hop/polymyxin composition, xanthohumol and the β form of the hop composition, also known as lupulone or β acid or β resin, have been found to be preferable in use, at least as presently advised, although the α resin, humulone, as well as iso derivatives, are also suitable for some uses. Exemplarily, the active ingredient in the hop composition may be isohumulone, lupulone or xanthohumol.

In the product form of the invention, the mixture of compositions that is utilized to treat the bacterial infection in the process form of the invention is separately identified. Here, again, polymyxin B is the presently preferred form of the polymyxin composition, and the α and β acids or resins and xanthohumol may be advantageously utilized as the hop composition that forms part of the mixture of compositions. The physical form of the mixture is related to the use to which the mixture is to be put. Thus, where the mixture is to be used as an eye drop, the mixture will usually take the form of a flowable liquid. However, where the mixture is to be applied to a wound to prevent bacterial infection, it may be preferable that it be in the form of a gel, cream or ointment.

As a consequence, it is a primary object of my invention to provide an effective treatment either for a bacterial infection already present, or as a protective means of warding off such an infection in a situation where there is a possibility that such infection will occur. These and other objects, features and advantages of the invention will be more apparent from a description of preferred embodiments of the invention and its attendant efficacy, as disclosed hereinafter.

DETAILED DESCRIPTION OF PREFERRED EMBODIMENTS

Various hop compositions, including the α and β resins, humulone and lupulone, and xanthohumol, were obtained from S. S. Steiner, Inc., of New York, N.Y. Quantities of polymyxin B were obtained from other commercial sources. In order to test the synergistic effect of mixtures of hops compositions and polymyxin B, two standard tests were used: the paper disc diffusion method, and the minimum inhibitory concentration (MIC) method.

The first test method to be applied was the paper disc diffusion susceptibility method. In this method a filter paper disc impregnated with a chemical is placed on agar, and the chemical will diffuse from the disc into the agar. If an organism is placed on the agar, it will not grow in the area around the disc if it is susceptible to the chemical. This area of no growth around the disc is known as the zone of inhibition. This disc diffusion method for antibiotic susceptibility is known as the Kirby-Bauer method. In testing the effectiveness of various antibiotics, all factors, e.g., the agar utilized, the depth of the agar, the amount of organism used, and incubation conditions, are maintained constant for the various organisms and antibiotics being tested. Under these conditions, the zone of inhibition will be the only variable, and the greater the zone, the more effective the antibiotic. The size of the zone of inhibition of the particular antimicrobial substance may also be influenced by the diffusion capability of that substance.

In performing the disc diffusion method tests, a bacterial suspension having an inoculum density of approximately $1 \times 10^8$ CFU/ml (colony forming units) was added to 10 ml trypticase soy agar at 46° C. It was mixed thoroughly by vortexing and then poured into a plastic Petri dish. After hardening of the agar, filter paper discs (φ7 mm.) made from Whatman filter paper No. 1 that had been impregnated by the manufacturer, Becton Dickinson, Inc., with the suitable antibiotic, were placed on the agar. In this series of tests the ability of each antibiotic per se to control the growth of the bacteria was measured.

Another series of agar containing Petri dishes was then prepared using the same bacteria and density thereof as had been prepared for the prior test series. However, here hop compounds were also present in the agar. The hop extract, either lupulone, humulone or xanthohumol, was dissolved in ethanol. While certain of the hop components are only slightly soluble in water, they are very soluble in ethanol. An ethanol control was prepared in the same way. The various hop fraction solutions were diluted in such a way that when added to the media solutions, the 10 ml. of agar poured into the Petri dish would contain in addition to the hop compound, exactly 1% of ethanol, which in a control was found to be non-inhibitory to the bacteria.

In each test, after an incubation period of 24 hours, a homogeneous lawn of bacteria developed throughout the disc, and a clear zone of inhibition was evident around those discs that contained inhibitory material. The size of the inhibition zones was measured to the nearest mm. The test results are demonstrated in the Tables below. Table 1 evidences the results of disc diffusion assays where the bacterium was *Staphlococcus saprophyticus*, a gram positive bacterium. As will be evident from the results of Table 1, Experiment 1, the control, which was the antibiotic per se, had no effect whatsoever on the bacterium, that is, there was no inhibition zone whatsoever around the disc of filter paper when polymyxin B was used alone. However, when the same polymyxin B was used in conjunction with 0.2 μg/ml of β-resin, the result was a zone of inhibition of 9 mm. This increase was unexpected and unanticipated.

The non-obviousness of the increase in the zone of inhibition when a combination of polymyxin and hops are used is made evident by the same test when performed using the same hop compound in conjunction with other antibiotics. The results were uniformly negative, i.e., there was no significant increase in the zone of inhibition when the resin lupulone was added in the same concentration in which it was added to the polymyxin composition. As the results of Table 1 show, neomycin per se had a zone of inhibition of 23 mm. When the lupulone was added, the zone increased to 25 mm. When the hop compound was added to streptomycin and erythromycin, the zones of inhibition remained constant, as they did with bacitracin. With penicillin, chloramphenicol and tetracycline, there was a decline in the zone.

The experiment was performed again in Experiment 2 and the results are tabulated in Table 1. It will there be seen that with all of the antibiotics other than polymyxin B, there was no significant change in the radius of the zone of inhibition when the β-resin was present. However, when the hop compound was added to the polymyxin B compound, the increase in the zone was dramatic: from zero to 8 mm.

TABLE 1

STAPHLOCOCCUS SAPROPHYTICUS

| ANTIBIOTIC | Experiment 1 | | Experiment 2 | |
|---|---|---|---|---|
| | Control | 0.2 µg/ml β-resin | Control | 0.2 µg/ml β-resin |
| POLYMYXIN | 0 | 9 | 0 | 8 |
| NEOMYCIN | 23 | 25 | 26 | 24 |
| STREPTOMYCIN | 15 | 15 | 15 | 14 |
| ERYTHROMYCIN | 23 | 25 | 23 | 23 |
| PENICILLIN | 41 | 39 | 37 | 35 |
| BACITRACIN | 0 | 0 | 0 | 0 |
| CHLORAMPHENICOL | 29 | 27 | 25 | 25 |

Another method of determining antimicrobial activity is to assess the Minimum inhibitory concentration (MIC) of the composition under test. The MIC is defined as the lowest concentration of the test compound where the bacterium shows no visible growth (Carson et al. 1995). This technique shows that at certain concentrations a test compound has no effect on the growth of a bacterium relative to the control. Thereafter, increased concentrations will have a limiting effect on growth, until the concentration is reached where no growth relative to the control is observed. That point of no growth is the minimum inhibitory concentration.

The MIC was determined by inoculating a bacterial suspension into 10 ml of Trypticase soy broth so as to provide an initial population of $1 \times 10^5$ CFU/ml with different concentrations of hop compounds ranging from 0.1 µg/ml to 10 µg/ml. A positive control with the bacterium alone was prepared as well as an ethanol control. The tubes were incubated at 37° C. for 24 hours and growth of the bacterium was determined by observing the change in turbidity. The results are tabulated in Table 2 below where, as indicated in the legend, the letter P stands for polymyxin B sulfate, the α and β symbols stand for the corresponding hop resins or bitter acids, and X stands for xanthohumol.

TABLE 2

Activity of antimicrobial agents on various microbes by combinations of hops constituents with polymyxin B sulfate

| X + P | P | α | β | X | α + P | β + P | X + P |
|---|---|---|---|---|---|---|---|
| exp 1 B. subtilis 10> | >20 <30 | >3 <10 | >1 <3 | >1 | 3 + 20 | no syn | 1 + 10 |
| exp 2 B. subtilis | >20 <30 | >3 <10 | >1 <3 | >1 | 1 + 10 | 0.3 + 10 | 1 + 10 |
| exp.1 B. megaterium | >100 | >5 <10 | >3 | 10 | >3 + 100 | 3 + 100 | 3 + 100 |
| exp. 2 B. megaterium | >100 | >5 <10 | 3 | 10 | >3 + 100 | no syn | 3 + 100 |
| exp 1 S. salivarius | >100 | >30 | >5 <10 | <10 | 30 + 100 | no syn | 10 + 100 |
| exp 2 S. salivarius | >100 | >30 | >5 <10 | <10 | 10 + 100 | 3 + 100 | 10 + 100 |
| exp 1 S. saprophyticus | >100 | >10 <30 | >1 <3 | >1 <10 | 3 + 30 | 1 + 30 | 1 + 30 |
| exp 2 S. saprophyticus | >100 | >10 <30 | >1 <3 | >1 <10 | 3 + 30 | 1 + 30 | 1 + 30 |

P = polymyxin B sulfate
α = alpha resin (or humulone)
β = beta resin (or lupulone)
X = xanthohumol
µg = micrograms To further explain the results of Table 2, utilizing B. subtilis as the bacterium, when polymyxin alone was utilized as the inhibitory agent, inhibition was achieved utilizing more than (>) 20 micrograms per milliliter but less than (<) 30 micrograms per milliliter concentration of solution. Following across the Table, and with regard to experiment 1, it required more than 3 but less than 10 µg per ml. to achieve minimum inhibition when the a resin was used alone, and more than 1 but less than 3 µg when the β resin was utilized. When xanthohumol alone was the inhibitory agent, more than 1 µg was required. With the addition of a hop resin to polymyxin B, the results for this same bacterium in the first series of experiments showed that complete inhibition was achieved using 3 parts of a resin and 20 parts of polymyxin. Inhibition was also achieved using 1 part of xanthohumol and 10 parts of polymyxin. When the B. subtilis test was repeated in experiment 2, the results were the same for the hop resins and polymyxin alone. However, inhibition was achieved with only 1 µg of alpha resin plus 10 µg per ml of polymyxin, and even less, 0.3 µg/ml β resin with 10 µg/ml polymyxin.

Each experiment for a specific bacterium was repeated once, so that there are two experiments for each bacterium. In a small minority of experiments no synergism was apparent, and these instances are duly reported. Yet each time that no synergism was reported, a complementary experiment on the same gram positive bacterium evidenced the presence of synergism. The overall conclusion, however, from the results tabulated in Table 4, is that when a hop compound is used in conjunction with polymyxin B, the amount of that anti-bacterial is greatly reduced and, therefore, that when various hop compounds are combined with polymyxin, the effect of such combination is to greatly reduce the quantity of polymyxin and/or hops necessary to inhibit the action of the bacteria that were the subjects of the experiments.

Since the filing of the original application Ser. No. 10/769,644, filed Feb. 2, 2004, of which application Ser. No. 10/991,221 is a continuation-in-part, additional MIC tests have been run using Polymyxin B with hop resins to determine the extent of the synergistic effect of the combination against gram negative bacteria. Those experiments have shown that the combination of Polymyxin B and lupulone had a synergistic effect against the following such bacteria: Pseudomo-

*nas fluorescens, Pseudomonas aeruginosa, Proteus vulgaris, Serratia marcescens, Proteus mirabilis* and *Enterobacter clocae*. Likewise, such additional MIC experiments have shown a significant synergistic effect of the same combination of ingredients used against *Staphylcoccus saprophyticus*, a gram positive bacterium.

Since the filing of application Ser. No. 10/991,221, the search for additional antibiotics that may or may not have a synergistic effect with a hop composition has been expanded. In accordance with those expanded experiments, two additional antibiotics that meet the test of synergism with hop compounds have been found: ciprofloxacin and tobramycin.

Table 3 shows the results of applying the disc diffusion test to four different bacteria, *S. saprophyticus, S. salivarius, B. subtilis* and *B. megaterium* with and without the addition of a hop compound. Both the β-acid lupulone and xanthohumol were tested, with the concentration of ciprofloxacin on the disk being 5 μg. The concentration of β-acid and xanthohumol is set forth in μg/ml. The zone of inhibition was measured in centimeters.

Table 4 is similar to FIG. 3 but tests tobramycin rather than ciprofloxacin. The same quantities of ingredients are used, except that the concentration of tobramycin on the disc is 10 μg. Both tables show a marked increase in the area of the zone of inhibition when a combination of the antibiotic and hop composition is used as opposed to antibiotic alone. The results of Tables 3 and 4 were confirmed by minimum inhibitory concentration tests similar to those tabulated in Table 2 hereinbefore.

TABLE 3

| β-acid | Exp #1 | Exp #2 | Avg | Xanthohumol | Expt #1 | Expt #2 | Avg |
|---|---|---|---|---|---|---|---|
| *S. saprophyticus* | | | | | | | |
| 0 | 1.0 | 1.0 | 1.0 | 0 | 0.9 | 1.0 | 0.95 |
| 3 | 1.5 | 1.3 | 1.4 | 3 | 1.3 | 1.7 | 1.5 |
| *S. salivarius* | | | | | | | |
| 0 | 0.6 | 0.8 | 0.7 | 0 | 0.8 | 0.8 | 0.8 |
| 30 | 1.3 | 1.1 | 1.2 | 10 | 1.9 | 2.1 | 2.0 |
| *B. subtilis* | | | | | | | |
| 0 | 1.1 | 0.9 | 1.05 | 0 | 1.1 | 0.9 | 1.0 |
| 3 | 1.5 | 1.4 | 1.45 | 3 | 2.0 | 1.7 | 1.85 |
| *B. megaterium* | | | | | | | |
| 0 | 1.0 | 0.7 | 0.85 | 0 | 0.8 | 0.7 | 0.75 |
| 3 | 1.5 | 1.0 | 1.25 | 3 | 1.6 | 1.9 | 1.75 |

TABLE 4

| β-acid | Exp #1 | Exp #2 | Avg | Xanthohumol | Expt #1 | Expt #2 | Avg |
|---|---|---|---|---|---|---|---|
| *S. saprophyticus* | | | | | | | |
| 0 | 0.9 | ND | 0.9 | 0 | 0.9 | 1.0 | 0.95 |
| 3 | 1.6 | ND | 1.6 | 3 | 1.5 | 1.5 | 1.5 |
| *S. salivarius* | | | | | | | |
| 0 | 0.6 | 0.5 | 0.55 | 0 | 0.6 | 0.5 | 0.55 |
| 30 | 0.7 | 0.6 | 0.65 | 10 | 1.4 | 1.3 | 1.35 |
| *B. subtilis* | | | | | | | |
| 0 | 1.1 | 0.9 | 1.0 | 0 | 1.1 | 0.9 | 1.0 |
| 3 | 1.4 | 1.2 | 1.3 | 3 | 1.6 | 1.4 | 1.5 |
| *B. megaterium* | | | | | | | |
| 0 | 0.8 | 0.6 | 0.7 | 0 | 0.8 | 0.6 | 0.7 |
| 3 | 1.1 | 0.8 | 0.95 | 3 | 1.1 | 1.0 | 1.05 |

It will thus be apparent that the combination of a hop compound, e.g., the alpha and beta resins or xanthohumol, or combinations thereof, together with polymyxin, ciprofloxacin or tabromycin, has a synergistic, antimicrobial effect on most bacteria, either gram positive or gram negative, provided that the hop compound and these selected antibacterials are used in combination. For reasons not determined, this synergistic effect is not apparent when hop compounds are used in combination with many other antibiotics. The synergistic effect results in a far more potent antibiotic preparation, and one that may well eliminate the need for combinations of antibiotics now on the market, such as a combination of polymyxin and bacitracin The combinations set forth herein as having synergistic or co-active effects have uses in many different forms, all of which are known to the art. If to be administered internally, the combination of an antibiotic and a hop compound may be swallowed in the form of a tablet or capsule. The combination is particularly useful for topical application in the form of an ointment or gel, as well as in other forms for ingestion for the treatment of intestinal disorders, all of which will be apparent to those of skill in this art. The combinations should also find particular application in fields where gram-positive bacteria are the pathogens to be overcome, such as in treating human and bovine mastitis.

It will also be recognized by those of skill in this art that certain modifications and alterations in the preferred embodiments of my invention will be obvious without departing from the spirit of the invention. As to all such obvious modifications, they are desired to be included within the purview of my invention, which is to be limited only by the scope, including equivalents, of the following, appended claims.

I claim:

1. A process for inhibiting bacterial infections in animals, comprising administering to said animals a pharmacologically effective amount of a mixture of a hop composition selected from the group consisting of humulone, lupulone, xanthohumol, and iso derivatives and mixtures thereof, and an antibiotic selected from the group consisting of ciprofloxacin and tobramycin, said mixture having a synergistic effect on said infections greater than the antibacterial effect of said antibiotic and said hop composition separately administered.

2. A process as claimed in claim 1, in which said infection is caused by gram positive bacteria.

3. A process as claimed in claim 1, in which said active ingredient is lupulone.

4. A process as claimed in claim 1, in which said active ingredient is isohumulone.

5. A process as claimed in claim 1, in which said active ingredient is tetrahydroisohumulone.

6. A process as claimed in claim 1, in which said active ingredient is xanthohumol.

7. A pharmacologically effective mixture of a hop composition selected from the group consisting of humulone, lupulone, xanthohumol, and iso derivatives and mixtures thereof, and an antibiotic selected from the group consisting of ciprofloxacin and tobramycin, said mixture having a synergistic effect greater than the antibacterial effect of said antibiotic and said hop composition separately administered.

8. A mixture as claimed in claim 7, in which said antibiotic is tobramycin.

9. A mixture as claimed in claim 7, in which said mixture is effective against gram positive bacteria.

10. A mixture as claimed in claim 7, in which said antibiotic is ciprofloxacin.

11. A mixture as claimed in claim 7, in which said active ingredient is lupulone.

12. A mixture as claimed in claim 10, in which said active ingredient is xanthohumol.

13. The mixture of compositions claimed in claim 7, in which the physical form of the mixture is selected from the group consisting of a liquid, gel, ointment and cream.

14. The mixture of compositions claimed in claimed 13, in which said form is a liquid and the mixture is used as an eye drop.

15. The mixture of compositions as claimed in claim 13, in which said form is an ointment and the mixture is used as a topical application to the skin.

16. A pharmacologically effective mixture of a hop composition, namely, lupulone, and an antibiotic selected from the group consisting of ciprofloxacin and tobramycin, said mixture having a synergistic effect greater than the antibacterial effect of said antibiotic and said hop composition separately administered.

* * * * *